United States Patent
Sørensen (12)

(10) Patent No.: US 11,806,904 B2
(45) Date of Patent: Nov. 7, 2023

(54) TIP PART ASSEMBLY FOR AN ENDOSCOPE

(71) Applicant: Ambu A/S, Ballerup (DK)

(72) Inventor: Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 48 days.

(21) Appl. No.: 17/013,519

(22) Filed: Sep. 4, 2020

(65) Prior Publication Data

US 2021/0068642 A1 Mar. 11, 2021

(30) Foreign Application Priority Data

Sep. 6, 2019 (EP) ..................................... 19195989
Sep. 6, 2019 (EP) ..................................... 19195995
(Continued)

(51) Int. Cl.
*A61B 1/05* (2006.01)
*A61B 1/00* (2006.01)
(Continued)

(52) U.S. Cl.
CPC ........ *B29C 45/14467* (2013.01); *A61B 1/009* (2022.02); *A61B 1/0011* (2013.01);
(Continued)

(58) Field of Classification Search
CPC . A61B 1/051; A61B 1/00094; A61B 1/00105; A61B 1/0011; A61B 1/00124;
(Continued)

(56) References Cited

U.S. PATENT DOCUMENTS 4,779,130 A   10/1988  Yabe
5,609,561 A    3/1997  Uehara et al.
(Continued)

FOREIGN PATENT DOCUMENTS

CN   201499375 U   6/2010
CN   104995907 B   5/2019
(Continued)

OTHER PUBLICATIONS

Extended search report in European Application No. 2019 1424, dated Feb. 1, 2021.
(Continued)

*Primary Examiner* — John P Leubecker
(74) *Attorney, Agent, or Firm* — Faegre Drinker Biddle & Reath LLP

(57) ABSTRACT

A method of manufacture of a tip part assembly for an endoscope, including: providing a bending section; providing a camera assembly including a camera module and a circuit board positioned at the proximal end of the assembly; providing a cup-shaped housing defining a distal end of the manufactured tip part assembly and including a circumferential wall extending between proximal and distal ends of the housing and a distal end wall positioned at the distal end of the housing, the circumferential wall and the distal end wall enclosing a spacing; inserting the camera assembly through the open proximal end of the housing so that the camera assembly is at least partly positioned within the spacing; and filling a liquid adhesive into the spacing through the open proximal end of the housing so that the camera assembly is at least partly embedded in the adhesive.

16 Claims, 7 Drawing Sheets

(30) Foreign Application Priority Data

Sep. 6, 2019 (EP) .................................. 19195996
Sep. 6, 2019 (EP) .................................. 19195998

(51) Int. Cl.

| | |
|---|---|
| A61B 1/06 | (2006.01) |
| B29C 45/14 | (2006.01) |
| A61B 1/015 | (2006.01) |
| A61B 1/018 | (2006.01) |
| A61B 1/07 | (2006.01) |
| A61B 1/005 | (2006.01) |
| B29K 105/00 | (2006.01) |
| B29L 31/00 | (2006.01) |
| A61B 1/307 | (2006.01) |

(52) U.S. Cl.
CPC ...... A61B 1/00094 (2013.01); A61B 1/00105 (2013.01); A61B 1/00124 (2013.01); A61B 1/015 (2013.01); A61B 1/018 (2013.01); A61B 1/051 (2013.01); A61B 1/0684 (2013.01); A61B 1/07 (2013.01); A61B 1/307 (2013.01); B29K 2105/0097 (2013.01); B29L 2031/7546 (2013.01)

(58) Field of Classification Search
CPC ......... A61B 1/005; A61B 1/015; A61B 1/018; A61B 1/0684; A61B 1/07; A61B 1/307; A61B 1/05; B29C 45/14467; B29K 2105/0097; B29L 2031/7546
See application file for complete search history.

(56) References Cited

U.S. PATENT DOCUMENTS

| | | | |
|---|---|---|---|
| 5,951,464 A * | 9/1999 | Takahashi | A61B 1/00165 600/176 |
| 7,662,094 B2 | 2/2010 | Iddan | |
| 7,833,151 B2 | 11/2010 | Khait et al. | |
| 8,414,480 B2 | 4/2013 | Kendale et al. | |
| 8,485,966 B2 | 7/2013 | Robertson | |
| 9,125,582 B2 | 9/2015 | Petersen | |
| 9,158,037 B2 | 10/2015 | Otsuka et al. | |
| 9,622,649 B2 | 4/2017 | Lin | |
| 9,814,371 B2 | 11/2017 | Segi et al. | |
| 9,866,738 B2 | 1/2018 | Kojima | |
| 10,025,088 B2 | 7/2018 | Handte et al. | |
| 10,188,275 B2 | 1/2019 | Sonnenschein et al. | |
| 2002/0193663 A1 | 12/2002 | Matsuura | |
| 2003/0113642 A1 | 6/2003 | Kami et al. | |
| 2004/0027459 A1 | 2/2004 | Segawa et al. | |
| 2004/0242963 A1 | 12/2004 | Matsumoto et al. | |
| 2005/0143659 A1 | 6/2005 | Saiga | |
| 2005/0222499 A1 | 10/2005 | Banik et al. | |
| 2005/0277340 A1 | 12/2005 | Gordon et al. | |
| 2006/0264704 A1 | 11/2006 | Fujimori et al. | |
| 2007/0027360 A1 | 2/2007 | Mitsuya | |
| 2007/0249907 A1 | 10/2007 | Boulais et al. | |
| 2008/0132760 A1 | 6/2008 | Takeuchi | |
| 2008/0242935 A1 | 10/2008 | Inoue | |
| 2008/0266441 A1 * | 10/2008 | Ichimura | H04N 5/2254 348/340 |
| 2008/0312504 A1 | 12/2008 | Kimoto | |
| 2009/0012358 A1 | 1/2009 | Ichihashi et al. | |
| 2009/0259101 A1 | 10/2009 | Unsai | |
| 2009/0260553 A1 | 10/2009 | Skovbo | |
| 2009/0295913 A1 * | 12/2009 | Sato | A61B 1/05 348/E7.085 |
| 2010/0016667 A1 | 1/2010 | Segawa et al. | |
| 2010/0185052 A1 * | 7/2010 | Chang | H04N 23/54 600/112 |
| 2011/0118549 A1 | 5/2011 | Han | |
| 2011/0288372 A1 | 11/2011 | Petersen | |
| 2012/0197081 A1 | 8/2012 | Kimura | |
| 2012/0220825 A1 | 8/2012 | Kimura | |
| 2012/0229615 A1 | 9/2012 | Kirma et al. | |
| 2013/0041223 A1 | 2/2013 | Kato | |
| 2013/0060083 A1 * | 3/2013 | Oku | A61B 1/0011 600/104 |
| 2013/0150667 A1 | 6/2013 | Mitamura et al. | |
| 2013/0172678 A1 | 7/2013 | Kennedy et al. | |
| 2013/0175720 A1 * | 7/2013 | Otsuka | G02B 23/243 264/1.32 |
| 2013/0271588 A1 | 10/2013 | Kirma et al. | |
| 2014/0073853 A1 | 3/2014 | Swisher et al. | |
| 2014/0100421 A1 | 4/2014 | Dejima et al. | |
| 2014/0142384 A1 | 5/2014 | Chung et al. | |
| 2014/0210976 A1 | 7/2014 | Lin | |
| 2014/0330081 A1 | 11/2014 | Imai | |
| 2015/0005580 A1 | 1/2015 | Petersen | |
| 2015/0062316 A1 * | 3/2015 | Haraguchi | A61B 1/00165 359/513 |
| 2015/0094534 A1 * | 4/2015 | Yamada | A61B 1/00112 600/110 |
| 2015/0148603 A1 * | 5/2015 | Holste | A61B 1/128 600/109 |
| 2015/0312457 A1 | 10/2015 | Kojima | |
| 2015/0358518 A1 | 12/2015 | Ishii et al. | |
| 2015/0378144 A1 | 12/2015 | Handte et al. | |
| 2016/0029879 A1 | 2/2016 | Ishikawa | |
| 2016/0051222 A1 | 2/2016 | Imahashi | |
| 2016/0209637 A1 | 7/2016 | Fujimori | |
| 2016/0235629 A1 | 8/2016 | Allyn et al. | |
| 2016/0287060 A1 | 10/2016 | Usuda et al. | |
| 2016/0313552 A1 | 10/2016 | Tomatsu | |
| 2017/0035279 A1 | 2/2017 | Fujii | |
| 2017/0108691 A1 | 4/2017 | Kitano | |
| 2017/0108692 A1 | 4/2017 | Kitano et al. | |
| 2017/0123200 A1 | 5/2017 | Suyama | |
| 2017/0245734 A1 * | 8/2017 | Kaneko | A61B 1/307 |
| 2017/0251914 A1 | 9/2017 | Kitano | |
| 2017/0325663 A1 | 11/2017 | Levy et al. | |
| 2018/0070803 A1 | 3/2018 | Mikami | |
| 2018/0153381 A1 | 6/2018 | Wei et al. | |
| 2018/0160893 A1 | 6/2018 | Truckai et al. | |
| 2018/0168041 A1 | 6/2018 | Govrin et al. | |
| 2018/0242822 A1 | 8/2018 | Hamazaki | |
| 2018/0317756 A1 | 11/2018 | Unsai | |
| 2019/0150711 A1 | 5/2019 | Chiu et al. | |
| 2019/0191968 A1 | 6/2019 | Tsumaru | |
| 2019/0282070 A1 | 9/2019 | Vilhelmsen et al. | |
| 2020/0163535 A1 | 5/2020 | Sekido | |
| 2020/0178766 A1 * | 6/2020 | Ichihara | A61B 1/00096 |
| 2020/0192078 A1 | 6/2020 | Spring et al. | |
| 2020/0225461 A1 | 7/2020 | Aizenfeld et al. | |
| 2020/0288953 A1 | 9/2020 | Sørensen et al. | |
| 2020/0297193 A1 | 9/2020 | Takahashi et al. | |
| 2021/0068634 A1 | 3/2021 | Sørensen | |
| 2021/0068640 A1 | 3/2021 | Sørensen | |
| 2021/0068641 A1 | 3/2021 | Sørensen | |
| 2021/0105386 A1 * | 4/2021 | Satake | H04N 7/183 |
| 2021/0153729 A1 * | 5/2021 | Kirma | H04N 5/2258 |
| 2022/0061630 A1 | 3/2022 | Yan et al. | |

FOREIGN PATENT DOCUMENTS

| | | |
|---|---|---|
| DE | 102010034623 A1 | 2/2012 |
| EP | 0306723 B1 | 3/1989 |
| EP | 0754429 B1 | 9/2004 |
| EP | 2110069 B1 | 3/2011 |
| EP | 2594307 A1 | 5/2013 |
| EP | 2692277 A1 | 2/2014 |
| EP | 2913850 A1 | 9/2015 |
| EP | 2692227 B1 | 8/2018 |
| EP | 2677736 B1 | 11/2018 |
| JP | 2004008638 A | 1/2004 |
| JP | 2008118568 A | 5/2008 |
| JP | 2010005277 A | 1/2010 |
| JP | 2011200397 A | 10/2011 |
| JP | 2011200399 A | 10/2011 |
| JP | 2011217887 A | 11/2011 |

(56) References Cited

FOREIGN PATENT DOCUMENTS

| | | |
|---|---|---|
| JP | 2012-201065 A | 10/2012 |
| JP | 2015002805 A | 1/2015 |
| JP | 2015058118 A | 3/2015 |
| JP | 5977892 B1 | 8/2016 |
| JP | 2016221316 A | 12/2016 |
| JP | 2017074207 A | 4/2017 |
| JP | 2018-093907 A | 6/2018 |
| WO | WO-0110295 A1 * 2/2001 | ........... A61B 5/0095 |
| WO | 2008/023965 A1 | 2/2008 |
| WO | 2010066790 A1 | 6/2010 |
| WO | 2014203604 A1 | 12/2014 |
| WO | 2018/022402 A1 | 2/2018 |
| WO | 2018/022418 A2 | 2/2018 |
| WO | 2019138462 A1 | 7/2019 |

OTHER PUBLICATIONS

Extended search report in European Application No. 1919 5995, dated Dec. 13, 2019.
Extended search report in European Application No. 1919 5996, dated Dec. 13, 2019.
Extended search report in European Application No. 1919 5998, dated Dec. 2, 2019.
Search Report issued by the European Patent Office, dated Jan. 3, 2020, for Application No. EP19195989, 9 pages.
Examination Report issued in EP 19 195 998.0, dated Jun. 28, 2023, 5 pages.
Examination Report issued in EP 20 191 424.9, dated Jul. 5, 2023, 5 pages.

* cited by examiner

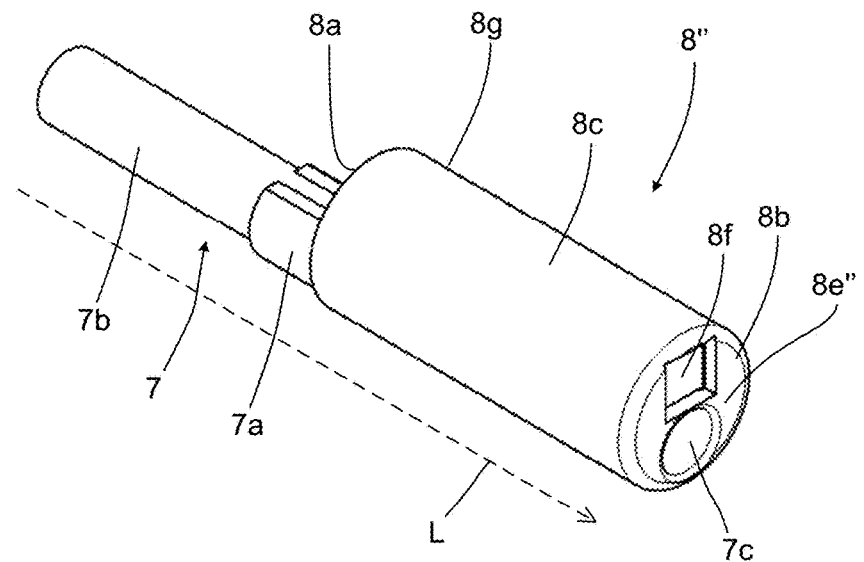
FIG. 4c
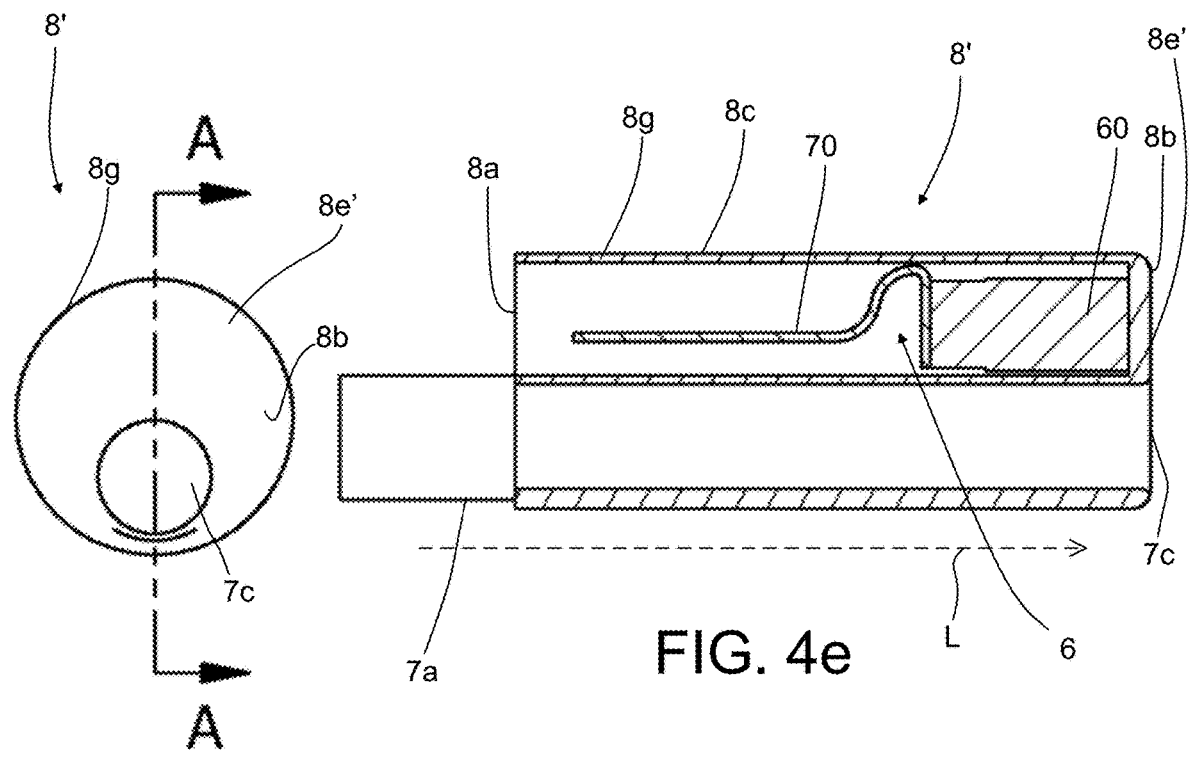
FIG. 4d
FIG. 4e

TIP PART ASSEMBLY FOR AN ENDOSCOPE

CROSS-REFERENCE TO RELATED APPLICATIONS

The present application claims priority from, and the benefit of, European Patent Application Nos. 19195989.9, 19195995.6, 19195996.4, and 19195998.0, filed Sep. 6, 2019, which applications are incorporated by reference herein in their entirety.

Commonly owned U.S. patent application Ser. Nos. 17/013,445, 17/013,463, and 17/013,488, filed concurrently with the present application, claim priority from European Patent Application Nos. 19195989.9, 19195995.6, 19195996.4, and 19195998.0, and are incorporated by reference herein in their entirety.

TECHNICAL FIELD

The present disclosure relates to endoscopes and more specifically to a tip part assembly for an endoscope.

BACKGROUND

Endoscopes are well known for visually inspecting difficult to access places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode, LED, or an optical fibre, may provide illumination.

Electrical wiring for the camera and other electronics, such as LED lighting accommodated in the tip part assembly at the distal end, run along the inside of the elongated insertion tube from the handle to the tip part assembly. Instead of using cameras, endoscopes may also be fibre-optic, in which case the optical fibres run along the inside of the elongated insertion tube to the tip part assembly. For some applications, a working or suction channel may run along the inside of the insertion tube from the handle to the tip part assembly, e.g. allowing liquid to be removed from the body cavity or allowing for insertion of surgical instruments or the like, into the body cavity. The suction channel may be connected to a suction connector, typically positioned at a handle at the proximal end of the insertion tube. For other applications, the working or suction channel may be omitted.

In order to be able to manoeuvre the endoscope inside the body cavity, the distal end of the endoscope may comprise a bending section with increased flexibility, e.g. an articulated tip part assembly allowing the operator to bend this section. Typically, this is done by tensioning or slacking steering wires also running along the inside of the elongated insertion tube from the articulated tip part assembly to a control mechanism of the handle.

A general desire in the field of endoscopy is to electrically insulate the insertion tube, and thus especially the tip part assembly, from the outside, so as to mitigate the risk of an insulation breakdown and a resulting excessive leakage current.

Another general desire in the field of endoscopy is to provide a tip part assembly which is liquid-sealed, so as to mitigate liquid ingress into the tip part assembly, and specifically into any electrical or optical components of the tip part assembly.

For some types of endoscopes, such as urethroscope, there is a desire to provide the tip part assembly of the endoscope with a smaller diameter or cross sectional extent, especially where the tip part assembly is to be inserted into narrower body cavities. In very narrow body cavities, even a reduction of 1 mm or less in the cross-sectional extent of a tip part assembly can have a noticeable effect on the comfort of the patient and may even make it possible to reach body areas not otherwise accessible. Providing a small size of the tip part assembly can especially be a challenge in cases where the endoscope comprises both a camera and a working channel extending through the tip part assembly since the camera and working channel are positioned one above the other within the tip part assembly, which takes up space in a radial direction of the tip part assembly.

U.S. Pat. No. 9,125,582 discloses an endoscope similar to the endoscopes mentioned above, where the majority of the components of the endoscope's tip part assembly are embedded in a material of the housing of the tip part assembly.

US Pub. No. 2008/0132760 discloses a tip part assembly for an endoscope comprising a compartment at the distal end of the tip part assembly, for accommodating a filler such as an adhesive for securing a portion of various components such us a light source or vision receptor of the tip part assembly within the compartment.

It is therefore desirable to provide a tip part assembly with a smaller outer diameter for an endoscope, such as an urethroscope, having electrically insulating properties and being mechanically stable.

SUMMARY

A first aspect of this disclosure relates to a method of manufacture of a tip part assembly for an endoscope, the tip part assembly comprising a tip part and having a proximal end and a distal end, the method comprising the steps of: a) providing a camera assembly of the tip part, the camera assembly including a camera module, the camera assembly having a distal end and a proximal end opposite the distal end, b) providing a cup-shaped housing having an open proximal end, the housing further having a distal end positioned oppositely from the proximal end and defining a distal end of the manufactured tip part assembly, the housing further comprising a circumferential wall extending between the proximal and distal ends of the housing and a distal end wall positioned at the distal end of the housing, the circumferential wall and the distal end wall enclosing a spacing, c) inserting the camera assembly through the open proximal end of the housing so that the camera assembly is at least partly positioned within the spacing, d) subsequent to step c), filling a liquid adhesive into the spacing through the open proximal end of the housing so that the camera assembly is at least partly embedded in the adhesive, and e) subsequent to step d), allowing or causing the adhesive to harden, whereby the adhesive attaches the housing and the camera assembly to each other.

In this way a tip part assembly of small dimensions, especially for urethroscopes, with an outer diameter of the circumferential wall of the housing of less than 3.3 mm or even smaller may be achieved. It has been realized that by providing a cup-shaped housing having an open proximal end and comprising a circumferential wall which together with a distal end wall encloses a spacing, a less complex housing structure may be achieved as the liquid adhesive may be filled into the spacing through the open proximal end of the housing, removing the need for providing a channel, port or the like in the housing for filling adhesive into the spacing. The less complex housing structure may allow the thickness of the circumferential wall of the housing to be reduced and so allow the outer diameter of the circumferential wall of the housing to be reduced. Therefore, the diameter or the cross-sectional extent of the housing and thus the tip part assembly can be reduced.

The tip part assembly may further comprise a bending section and the method comprise the steps: providing the bending section, the bending section having a distal end segment, and subsequent to step e), adjoining the distal end segment of the bending section and the proximal open end of the housing.

The camera assembly may further include a circuit board, the circuit board being positioned at the proximal end of the camera assembly.

The cup-shaped housing of the tip part assembly ensures that a minimum insulation thickness is present on all sides of the components housed within the spacing, this may improve or provide a more secure electrical insulation around the camera module, circuit board, image sensor and electrical connections.

The adhesive filled into the housing from the open proximal end thereof may provide greater robustness, mechanical stability and/or rigidity of the tip part assembly. A better attachment/fixation of the components within the housing, which may be of particular importance during operation of the endoscope where wires or cables may be pulled, and stress or pulling in the circuit board may occur, especially during bending of the bending section may also be achieved.

The term "endoscope" may be defined as a device suitable for examination of natural and/or artificial body openings, e.g. for exploration of a lung cavity. Additionally, or alternatively, the term "endoscope" may be defined as a medical device.

The term "cup-shaped" may be defined as the general hollow shape of a cup without a handle.

The circumferential wall may be an outer or exterior wall and may include an outer surface of the tip part assembly for facing the environment. Potentially, no parts of or only a sleeve of the tip part assembly are positioned outside an outer circumference of the circumferential wall.

In this specification, a proximal-distal direction may be defined as an axis extending along the parts of the insertion tube of the endoscope. Adhering to the definition of the terms distal and proximal, i.e. proximal being the end closest to the operator and distal being the end remote from the operator. The proximal-distal direction is not necessarily straight, for instance, if the insertion tube is bent, then the proximal-distal direction follows the curvature of the insertion tube. The proximal-distal direction may for instance be a centre line of the insertion tube.

The distal end of the tip part assembly may form a distal end of the endoscope.

The camera assembly may be a sub-assembly of the tip part and may comprise a camera module which may include an image sensor, and a camera module housing in which the camera module may be arranged. Outer surfaces of the camera housing may be substantially box-shaped and/or parallelepipedal. The camera assembly may be fully embedded in the adhesive, potentially except for a distal lens thereof. The camera assembly may comprise at least one lens or a lens stack with two, three or more lenses. The lens stack may comprise a distal lens, i.e. the lens thereof positioned closest to the distal end of the tip part assembly. Similarly, the lens stack may comprise a proximal lens i.e. the lens positioned closest to the proximal end of the tip part assembly. The camera assembly may be at least partly housed in the housing.

The lens stack may be positioned distally of or in front of the image sensor. The camera module may further comprise a lens barrel which may hold and encase the lens stack. The lens stack may be stacked and/or the lens barrel may extend in the longitudinal direction.

The at least one lens, potentially the plurality of lenses, may be of one or more types chosen from the group consisting of: concave, convex, plano-concave, plano-convex, bi-convex, bi-concave.

The cup-shape of the cup-shaped housing may be formed by the circumferential wall and the distal end wall enclosing a spacing where a proximal end of the housing is open and a distal end of the housing is closed. The housing may be tubular and/or cylindrical or substantially cylindrical and/or circular cylindrical or substantially circular cylindrical. The housing may provide electrical insulation and/or water tightness around the circuit board and electrical connections within the housing and may form a mold or container for adhesive and/or potting material poured or injected into the housing. The housing may ensure that a minimum insulation thickness is present on one or more sides or all outer surfaces of the tip part assembly. When an adhesive or a potting material is present in the housing, this may provide greater robustness, mechanical stability and/or rigidity of the tip part, and/or better attachment/fixation of components within the housing. This may be advantageous since wires or cables may be pulled during operation of the endoscope, pulling also in the circuit board, especially during bending of a bending section of the tip part assembly.

The housing may be an outer or exterior housing which may be exterior with respect to elements housed or enclosed therein, such as the camera assembly, wires, electrical components, LEDs, and the like.

The liquid adhesive may be of low dynamic viscosity, such as a dynamic viscosity below or equal to 200, 150, 120, 110 or 100 cP (centipoise, which is equal to mPa*s). This may ensure that the adhesive reaches all corners or substantially all corners of a free volume of the spacing.

The adhesive may be poured into the spacing through the open proximal end of the housing. The adhesive may be injected into the spacing through an injection needle or a nozzle inserted through or positioned above the said open proximal end of the housing.

A predefined amount of adhesive corresponding to a desired amount of adhesive in the spacing may be measured off during filling. Alternatively, or additionally, an upper or top level of the adhesive may be measured during filling to ensure a predefined amount of adhesive is filled into the housing.

The adhesive may be or may function as a potting material and may be unhardened or uncured when filling out the spacing. The adhesive may be cured after being filled into the spacing.

The adhesive may have electrically insulating properties and/or may be a potting material, e.g. such as disclosed in JP2011200399.

The adhesive and/or potting material may comprise or consist of or substantially consist of polyurethane adhesives, silicone adhesives, UV adhesives, resins, adhesive resins, thermosetting plastics, silicone rubber gels, polyurethane, silicone or combinations thereof.

The adhesive and/or potting material may be heat cured, chemically cured, radiation cured (such as UV light cured) or moisture cured etc.

The bending section may comprise a number of hingedly interconnected segments including the distal end segment, a proximal end segment, and a plurality of intermediate segments positioned between the proximal end segment and the distal end segment. At least one hinge member may interconnect adjacent segments with each other. The bending section may be a section allowing the tip part assembly to bend relative to an insertion tube, potentially so as to allow an operator to manipulate the tip part assembly while inserted into a body cavity of a patient. The bending section may be molded in one piece or may be constituted by a plurality of molded pieces.

The bending section may or may not be attached to the housing by introducing a holder ring therebetween as is known in the art. A second adhesive (which may be the same material as the adhesive in the spacing) may be separately applied to attach the bending section end segment to the housing or, if a holder ring is present, to attach the distal end segment and the housing to the holder ring.

The tip part assembly may further include a working channel extending through the spacing of the housing to a hole or an opening in the end wall. The working channel may be molded in one piece with the housing or may be provided separately from the housing. The working channel may extend into and/or through the distal end segment and/or the bending section.

The working channel may be tubular or substantially tubular and/or have a circumferentially extending, potentially cylindrical or circular cylindrical or substantially cylindrical or circular cylindrical, outer wall enclosing a working channel spacing. A material thickness of the tubular or substantially tubular wall may be less than or equal to 0.2 mm or less than or equal to 0.15 mm.

The working channel may have an inner diameter of 0.8 to 2 mm or 1 to 1.6 mm or 1 to 1.4 mm. A wall thickness of a circumferential wall of the working channel may be 0.1 to 0.5 mm.

The working channel may comprise a chamfered portion, which may face at least a part of the camera assembly. The chamfered portion may, additionally or alternatively, be provided as a canted-off portion, a bevelled portion, or the like. The chamfered portion may be abutting at least part of the camera assembly or may be positioned with a distance to the camera assembly.

The chamfered portion may be part of the circumferential wall of the working channel, where a such is provided, or may be formed in one piece with the wall. The wall thickness of the chamfered portion of the circumferential wall may thus be smaller than along at least one other portion of the circumferential wall.

The working channel may allow liquid to be removed from a body cavity and/or allow insertion of surgical instruments or the like into the body cavity. The working channel may be provided as a channel extending from a proximal end of an endoscope to a distal end of the endoscope to guide a tool and/or to provide suction. A connector and/or a connecting portion may be provided at the proximal end of the endoscope to allow insertion of a tool into the working channel and/or to allow suction to be applied to the working channel. In some embodiments, the working channel comprises a built-in or integrated tool at or in the distal tip part assembly. Such a tool may be suitable for grabbing, taking, and/or holding elements in a part of a patient, in which the endoscope tip part is arranged during use.

The working channel may be at least partly housed in the housing. The working channel or a part thereof may be in one piece with the housing and/or may be provided as a separate part. The working channel may comprise a first portion potentially provided in one piece with the housing, and a second portion interconnected with the first portion. The second portion may be provided as a flexible tube and may be interconnected to the first portion by means of an adhesive. The working channel of the tip part assembly and the circumferential wall may be formed in one piece.

Especially if no working channel is present, the housing end wall and circumferential wall optionally do not comprise any holes or openings. If the tip part assembly includes a working channel, a working channel hole may be provided, potentially as the only or single hole or opening, in the end wall. Positioning a working channel in a hole in the end wall does not carry the same risk of adhesive flowing out at a periphery of the hole since adhesive residuals at a working channel distal end opening are not as disruptive as is the case for adhesive residuals at the camera assembly (and LEDs, cf. below).

The end wall may be formed integrally with or in one piece with the circumferential wall.

The tip part assembly may further include at least one light-emitting diode, LED, for illuminating a target, which may be positioned in the spacing before filling adhesive into the spacing. The LED(s) may be embedded or substantially embedded in the adhesive. The circuit board may include an arm leading to and connected to the LED. The circuit board may include an arm leading to and connecting to each at least one LED.

The tip part assembly may also include one or more light guides and/or LED lenses for guiding light from respective LED(s) to e.g. a front or distal end surface or end wall of the tip part assembly and/or a housing thereof. The light guide(s) may extend from the distal end of the tip part assembly to a respective LED or a respective set of LEDs. In some embodiments, the light guides are made from a transparent material. The light guide(s) may be molded and/or may comprise a portion abutting the camera assembly and/or be arranged in front of the lens stack.

The LEDs may comprise a light emitting surface. The light emitting surface(s) may emit light in the proximal-distal direction. The light emitting surface(s) may be positioned in abutment with the housing, where this is provided, or in abutment with one or more light guides.

If no light guide is present, the LED may be positioned adjacent a proximal end surface of the distal end wall, in which case the adhesive may not be present between a front surface of the LED and a proximal end of the light guide, or between a front surface of the LED and a proximal surface of the end wall. The light guide may be at least partly embedded in the adhesive. The light guide may include a light shield, in particular on a surface of the light guide facing the camera assembly. The light shield may be provided as a layer of color or a material cladding with material having a low refraction index on said surface.

The method step of providing the housing may include the step of molding the housing, which may occur before the assembly steps of the method. Molding of the housing may occur as a two-component molding in which two different materials are molded in the same mold. For example, the end wall of the housing may be molded in a first material, which may be transparent, and the circumferential wall may be molded in a second, different material, which may be non-transparent and may include higher adhesive compatibility with the adhesive. Alternatively, the circumferential wall can be manufactured separately from the end wall. For example, the circumferential wall and the end wall can be molded separately, or the end wall can be molded, and the circumferential wall extruded. In this case, the circumferential wall and the end wall can be adhered to each other by means of an adhesive.

The term "higher adhesive compatibility" in the context of this specification, may be understood as a material providing a higher adhesive bond strength, being compatible with a wider range of adhesives, having a higher mechanical and/or chemical stability with adhesives.

The circuit board may be a printed circuit board (PCB) or a flexible printed circuit (FPC). The housing may be attached to the circuit board by means of the hardened adhesive. The entire or substantially the entire circuit board may be embedded in the adhesive.

FPCs may, throughout this specification, be a single- or double-sided flexible circuit or a rigid-flex circuit, and may comprise one or more layers of conductive material and two or more layers of insulating material, and/or may be a flexible flat cable having one or more conductors. In some embodiments, the FPC may be connected to a second flexible printed circuit and/or to a printed circuit board (PCB), e.g. comprising one or more cupper layers and one or more layers of insulating materials, such as layers of a FR-4 (flame retardant) composite material.

An electronic cable or electronic wires for connecting the circuit board to other parts of the endoscope may be at least partly embedded in the adhesive.

The camera assembly and potentially one or more LEDs may first be attached to one or more holders, where the interconnected holder(s) and camera assembly and potentially LED(s) are then positioned in the housing before filling in the adhesive.

The circuit boards and potentially wires for connecting the circuit board to other parts of the endoscope may be attached to the camera module and potentially the LEDs before or after positioning of the holder(s) and camera assembly and potentially the LED(s) in the housing.

The adhesive may fill out or substantially fill out all spacing volumes around the camera assembly, potentially except camera assembly holder(s) and/or a distal end or front surface of the camera assembly or a distal lens thereof. The adhesive may similarly fill out or substantially fill out all spacing volumes around the LED(s), potentially except LED holder(s) and/or a distal end or front surface of the LED(s). Alternatively, one or more holders may include one or more separation parts that may separate one or more separate spacing volumes so that the adhesive does not flow into these separate spacing volumes; this may be of advantage if it is desired to avoid that the adhesive flows in front of a camera assembly distal lens or an LED.

This may provide precise and repeatable positioning of the camera assembly and potentially the LEDs in the housing.

At least during step e) the housing may be positioned so that the proximal open end faces upwards. This may also be the case in step f).

This may allow easy filling of the adhesive into the housing as the filling of the adhesive may be aided by gravitational force.

An entire free volume of the spacing may be substantially filled up with the adhesive up until an upper adhesive level. Alternatively, an entire free volume of the spacing may be filled up until an upper adhesive level.

The adhesive may propagate to fill up also spacing volumes around the camera assembly and potentially the LED(s), even at a distal end of, i.e. in front of, the camera assembly and potentially the LED(s). With no empty spacings inside, the tip part assembly will be more rigid and less prone to being destroyed if forces are applied to it, e.g. if the tip part is accidentally dropped.

This may provide a robust and/or mechanically stable tip part assembly. It may also ensure that a correct and/or sufficient amount of adhesive is filled into the housing to attach the components therein to each other.

An outer diameter of the circumferential wall of the housing may be less than 3.3 mm.

In case the circumferential wall is not circular in cross section, this distance may instead be a largest cross sectional extent of the circumferential wall. The outer diameter or largest cross sectional extent of the circumferential wall of the housing may be less than 3.2, 3.1, 3.0. 2.9, 2.8, 2.7, 2.6 or 2.5 mm.

This may provide a tip part assembly with a small outer diameter and/or a tip part assembly with a small outer diameter of a circumscribed circle in a cross-section of the tip part assembly. This may improve comfort compared to endoscopes with tip part assemblies with larger outer diameters. It may also allow the tip part assembly to be used in applications which were previously inaccessible due to the outer diameter of tip part assemblies being too large.

A distal surface of a distal lens of the camera assembly may be positioned adjacent or abutting a proximal surface of the housing end wall.

This may provide increased security regarding tightness between the camera assembly, potentially a distal lens thereof, and the housing. Furthermore, the adhesive may tend to pour or flow out of the hole if the camera assembly, such as a distal lens thereof, is positioned in such a hole in the end wall. Adhesive spilling out here may flow to a surface of a distal surface of the camera assembly, potentially on or in front of a distal lens thereof, and distort the camera view in use.

Similarly, a distal and/or light emitting surface of an LED of the tip part assembly may be positioned adjacent or abutting a proximal surface of the housing. This proximal surface may be a proximal surface of the housing end wall or of a light guide. This may provide increased security regarding tightness between the LED and the housing. Furthermore, the adhesive may have a tendency to pour or flow out of the hole if the LED is positioned in such a hole in the end wall. Adhesive spilling out here may flow to a surface of a distal or front surface of the LED and distort light from the LED.

For both the camera assembly and LED, if no corresponding hole is provided in the end wall, and the camera assembly, potentially a distal lens thereof, and/or LED(s) is/are instead positioned with a distal surface adjacent to a proximal surface of the housing as described above, a layer of adhesive may be present between the distal lens or LED and the proximal surface of the housing. This layer of adhesive may be well-defined or have a uniform or substantially uniform thickness along the adjacent surfaces. This may minimize distortion of light shining through the layer of adhesive. Alternatively, the camera assembly, potentially a distal lens thereof, or LED distal surface abuts the housing proximal wall so that no or substantially no adhesive is present therebetween. A low viscosity adhesive as disclosed herein may be advantageous also to provide a thin layer of glue in this context. The layer of glue may be injected first directed against a volume between the distal and proximal surfaces after which the remaining adhesive is filled into the housing. Alternatively, the end wall comprises a hole for a distal lens of the camera assembly and/or an LED and/or an LED light guide, which is then positioned in the hole upon positioning of the camera assembly in the spacing.

The circumferential wall and/or the end wall of the housing may be transparent.

In this context, transparent is meant to describe that light or a suitable amount of light according to the purpose, i.e. light into the camera assembly and/or light from LED(s), is able to pass through the wall.

The housing may comprise or consist or substantially consist of a transparent plastic or plastic polymer material, such as: a polycarbonate (PC) polymethylmethacrylate (PMMA), Polyethylene Terephthalate (PET), Amorphous Copolyester (PETG), Polyvinyl Chloride (PVC), Liquid Silicone Rubber (LSR), Polyethylene (PE), Fluorinated Ethylene Propylene (FEP), Styrene Methyl Methacrylate (SMMA), Styrene Acrylonitrile Resin (SAN) and/or Methyl Methacrylate Acrylonitrile Butadiene Styrene (MABS). This may remove the need for a window or opening for the camera module and/or LED(s) in the circumferential wall and/or the end wall to allow the camera assembly to register a target area of the endoscope and/or for light emitted from the LED(s) to illuminate a target area of the endoscope. This again may provide a housing that is more resistant to ingress of liquid compared to a housing with an opening in the circumferential wall and/or end wall. Similarly, improved electrical insulation of the components in the housing may be achieved compared to a housing with an opening in the circumferential wall and/or end wall. Compared to a tip part assembly with holes, openings, and/or windows in the circumferential wall and/or end wall, it may provide a tip part assembly that is easier to manufacture as adhesive may not run or spill out of the holes, openings, and/or windows.

The term "target" or "target area" in the context of this specification, may be understood as an object or area of interest that the tip part assembly of the endoscope is being used to analyze.

The tip part assembly may further include one or more light guides and/or LED lenses. The tip part assembly may further include one or more light guides and/or LED lenses in one piece with housing. One or more of these light guides and/or LED lenses may be molded in one piece with the housing; in that case, at least these parts of the housing may be transparent.

This may provide unobstructed and well-defined guidance of light emitted by the LED(s) towards a target area.

Step c) may include molding the housing in a two-component molding process, wherein the end wall of the housing is molded in a first material, which is transparent, and the circumferential wall is molded in a second, different material, which is non-transparent.

This may allow the camera assembly to register a target area through the transparent end wall whilst the circumferential wall with higher adhesive compatibility allows secure adhesive attachment of the camera assembly to the housing. This may also remove the need for an opening or window for the camera assembly or LED(s) in the end wall or circumferential wall.

Similarly, it may allow an LED to illuminate a target area through the transparent end wall, whilst the circumferential wall with higher adhesive compatibility allows secure adhesive attachment of the LED to the housing.

The second material may include a higher adhesive compatibility.

A wall thickness of the circumferential wall may increase from the proximal end of the housing towards the distal end of the housing.

Hereby, a more secure electrical insulation and/or mechanical stability may be provided since the wall thickness may be provided to be larger in an area of the endoscope that may be most exposed or stressed during use.

A second aspect of this disclosure relates to a tip part assembly for an endoscope, the tip part assembly comprising a tip part and having a proximal end and a distal end, the tip part assembly comprising: a tip part including a cup-shaped housing and a camera assembly positioned at least partly within a spacing of the housing, the camera assembly being attached or adhered to the housing by means of a hardened adhesive positioned within the spacing, the camera assembly being at least partly embedded in the adhesive, wherein the camera assembly includes a camera module, the camera assembly having a distal end and a proximal end opposite the distal end, wherein the housing has an open proximal end and a distal end positioned oppositely from the proximal end, the distal end of the housing defining a distal end of the tip part assembly, the housing further comprising a circumferential wall extending between the proximal and distal ends of the housing and an end wall positioned at the distal end of the housing, the circumferential wall and the distal end wall enclosing the spacing, wherein the adhesive is provided separately from the housing.

This may provide a tip part assembly with a small outer diameter and/or a tip part assembly with a small outer diameter of a circumscribed circle in a cross-section of the tip part assembly. It may further provide a robust tip part assembly.

The tip part assembly may further comprise: a bending section having a distal end segment, and wherein the distal end of the bending section and the proximal open end of the housing are adjoined to each other.

The camera assembly may further include a circuit board, the circuit board being positioned at the proximal end of the camera assembly.

Any features of the embodiments of the method according to this disclosure may also be present in the tip part according to this disclosure.

An entire volume of the spacing not preoccupied by the camera assembly and potential further components positioned in the spacing may be substantially filled up with the adhesive up until an upper adhesive level, the upper adhesive level may be a level of the adhesive towards the proximal end of the tip part assembly.

Alternatively, an entire volume of the spacing not preoccupied by the camera assembly and potential further components positioned in the spacing is filled up with the adhesive up until an upper adhesive level, the upper adhesive level being a level of the adhesive towards the proximal end of the tip part assembly.

Alternatively, this could be defined as there substantially not being any air pockets present within the spacing up until an upper adhesive level.

Alternatively, this could be defined as there not being any air pockets present within the spacing up until an upper adhesive level.

The adhesive may propagate to fill up also spacing volumes around the camera assembly and potentially the LED(s), even at a distal end of, i.e. in front of, the camera assembly and potentially the LED(s). With no empty spacings inside, the tip part assembly will be more rigid and less prone to being destroyed if forces are applied to it. E.g. if the tip part is accidentally dropped.

"Provided separately from" may include or may mean that the adhesive and the housing are not integral or are not in one piece or are not molded in one piece with each other.

If the housing is positioned upright with the housing proximal end facing upwards, the adhesive level is the level that the adhesive reaches in an upward direction.

An outer diameter of the circumferential wall of the housing may be less than 3.3 mm.

In case the circumferential wall is not circular in cross section, this distance may instead be a largest cross sectional extent of the circumferential wall. The outer diameter or largest cross sectional extent of the circumferential wall of the housing may be less than 3.2, 3.1, 3.0. 2.9, 2.8, 2.7, 2.6 or 2.5 mm. This may allow the endoscope to be used in places otherwise not accessible due to size limitations.

A distal surface of a distal lens of the camera assembly may be positioned adjacent or abutting a proximal surface of the housing end wall.

The circumferential wall and/or the end wall of the housing may be transparent.

A third aspect of this disclosure relates to an endoscope comprising a tip part assembly manufactured according to the first aspect of this disclosure or a tip part assembly according to the second aspect of this disclosure.

The endoscope may comprise a control element. The control element may be configured to allow an operator to control a tip part assembly of the insertion tube by at least one steering wire. The control element may allow bending the tip part assembly in at least one direction, potentially in two directions, the two directions potentially being opposite. The control element may be accommodated in an operating handle. The control element may include a lever allowing an operator to control the control element. The lever may extend outwardly from the control element, potentially through an operating handle. The control element may be in the form of a roller or a roller disc.

The endoscope may comprise an operating handle. The operating handle may be suitable for allowing an operator to grip and to operate the endoscope, potentially with one hand. The operating handle may comprise a handle housing arranged at a proximal end of the insertion tube. The handle housing may accommodate the control element.

The insertion tube and/or a distal end thereof and/or the tip part assembly thereof may be suitable for insertion into a body cavity, potentially a kidney, through a body opening, potentially a urinary passage or a urethra. The body may be a natural and/or artificial body, potentially a human body. The insertion tube may extend from the operating handle towards a distal end of the endoscope.

Additionally or alternatively, the endoscope may form part of a system for visually inspecting inaccessible places such as human body cavities, the system further comprising a monitor. The endoscope may be connectable to the monitor, and the monitor may allow an operator to view an image captured by the camera assembly of the endoscope.

A person skilled in the art will appreciate that any one or more of the above aspects of this disclosure and embodiments thereof may be combined with any one or more of the other aspects of the disclosure and embodiments thereof.

BRIEF DESCRIPTION OF DRAWINGS

The tip part assemblies and methods will now be described in greater detail based on non-limiting exemplary embodiments and with reference to the drawings, on which:

FIG. 4c shows a perspective view of a third embodiment of a tip part assembly of FIGS. 1a and 1b, FIG. 4d shows a view onto the distal end of the tip part assembly of FIG. 4b, FIG. 4e shows a section view A-A of the tip part assembly of FIG. 4d.

DETAILED DESCRIPTION

Figure 1A:
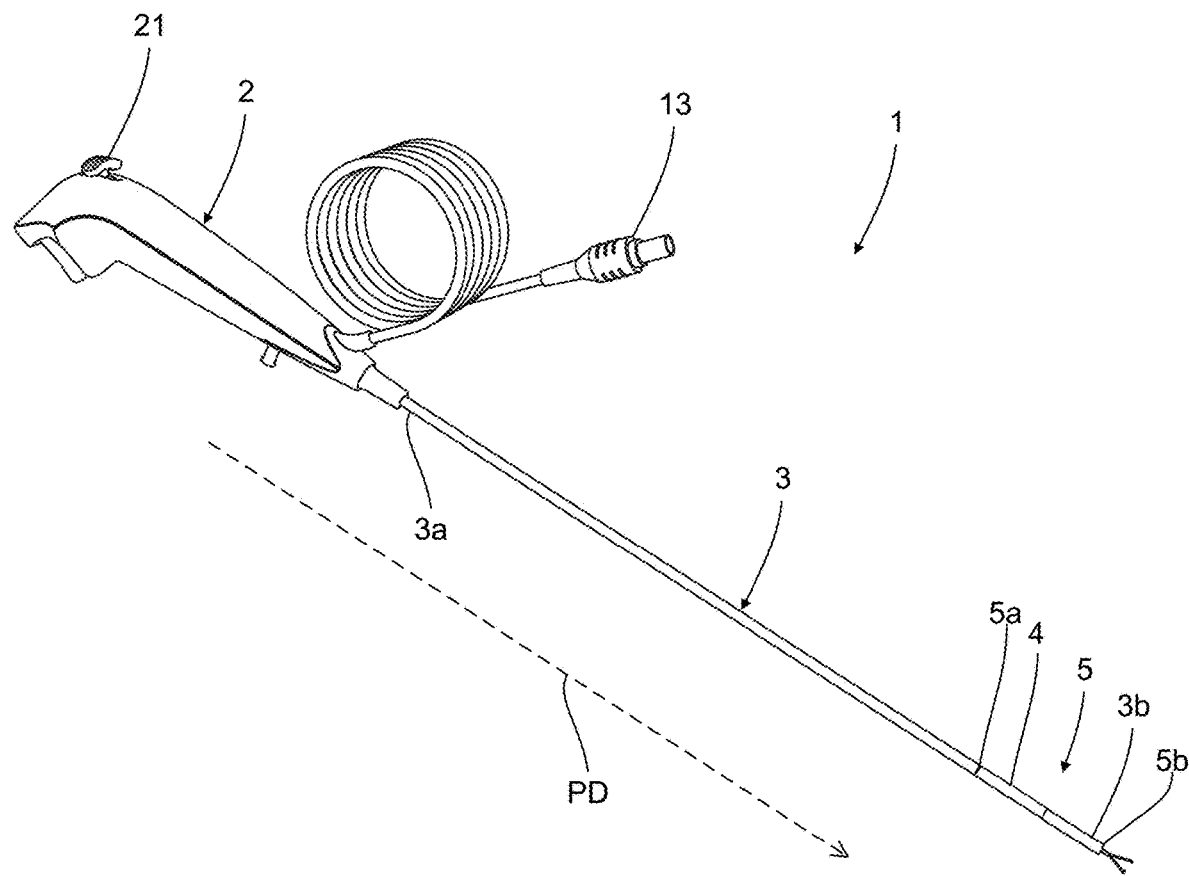
FIG. 1a shows a perspective view of an endoscope in which a tip part assembly according to the present disclosure is implemented.

Referring first to FIG. 1a, an endoscope 1 is shown. The endoscope is disposable, and not intended to be cleaned and reused. The endoscope 1 comprises an elongated insertion tube 3. At a proximal end 3a of an insertion tube 3 of the endoscope 1, an operating handle 2 is arranged. The operating handle 2 has a control lever 21 for manoeuvring a tip part assembly 5 at a distal end 3b of the insertion tube 3 by means of a steering wire and bending section 4. A camera assembly 6 is positioned in the tip part assembly 5 and is configured to transmit an image signal through a monitor cable 13 of the endoscope 1 to a monitor 11.

The tip part assembly 5 has a proximal end 5a for being connected to other parts of the endoscope 1, and a distal end 5b positioned oppositely from the proximal end 5a forming the distal end 3b of the endoscope 1.

Figure 1B:
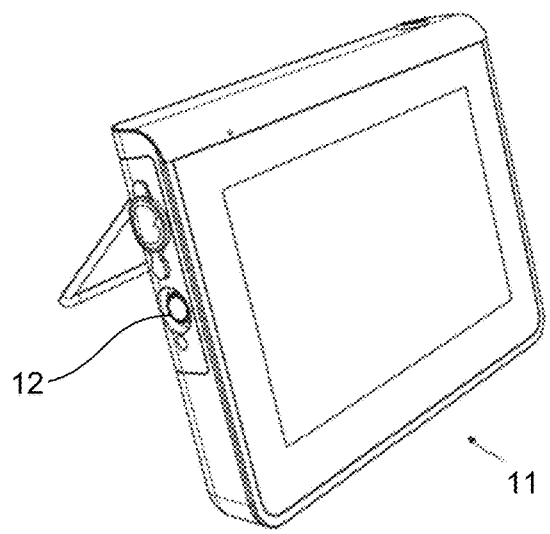
FIG. 1b shows a perspective view of a monitor to which the endoscope of FIG. 1a is connected.

In FIG. 1b, a monitor 11 is shown. The monitor 11 may allow an operator to view an image captured by the camera assembly 6 of the endoscope 1. The monitor 11 comprises a cable socket 12 to which a monitor cable 13 of the endoscope 1 can be connected to establish a signal communication between the camera assembly 6 of the endoscope 1 and the monitor 11.

The proximal-distal direction PD is a direction extending along the parts of the insertion tube 3 of the endoscope 1.

Figure 2:
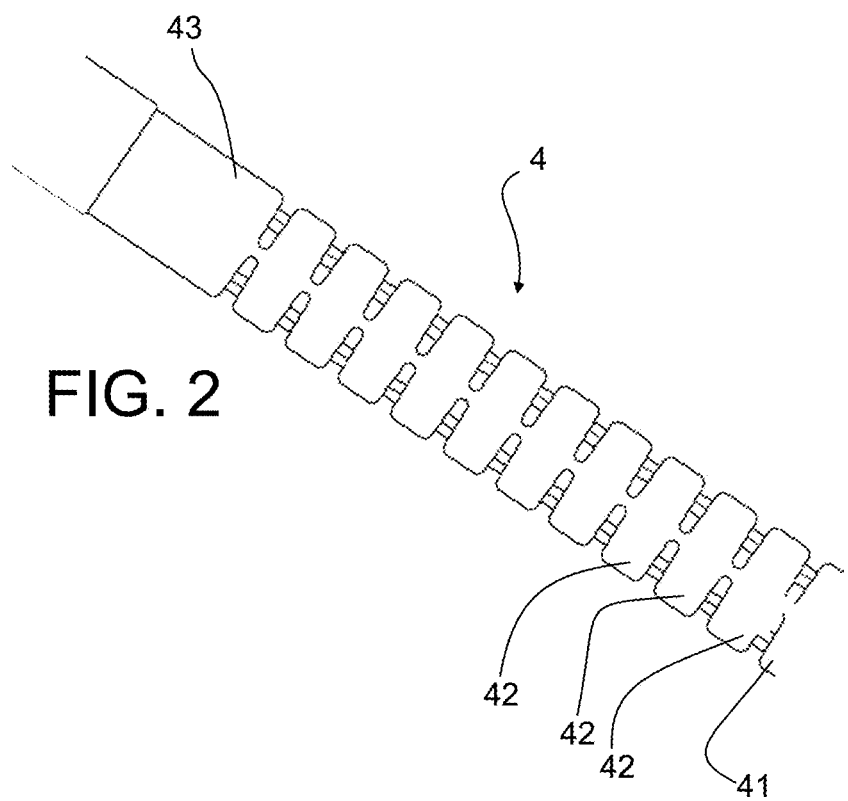
FIG. 2 shows a side view of a bending section of the endoscope of FIG. 1a and FIG. 1b.

Turning to FIG. 2, a side view of the bending section 4 is provided. The bending section 4 allows the tip part assembly 5 to bend relative to the insertion tube 3, so as to allow an operator to manipulate the tip part assembly 5 while inserted into a body cavity of a patient. The bending section 4 is molded in one piece, but may alternatively be constituted by a plurality of molded pieces. The bending section 4 comprises a number of hingedly connected segments including a distal end segment 41, a proximal end segment 43, and a plurality of intermediate segments 42 positioned between the distal end segment 41 and the proximal segment 43. The distal end segment 41 is adapted for being connected and/or attached to a housing of a tip part assembly, such as the housing 8, 8', 8" of FIGS. 4a-4f at a proximal end 8a of the housing 8, 8', 8". A second adhesive (which may be the same material as the adhesive 80 in the spacing) is separately applied to adjoin the bending section end segment 41 to the housing 8, 8', 8".

Figure 3:
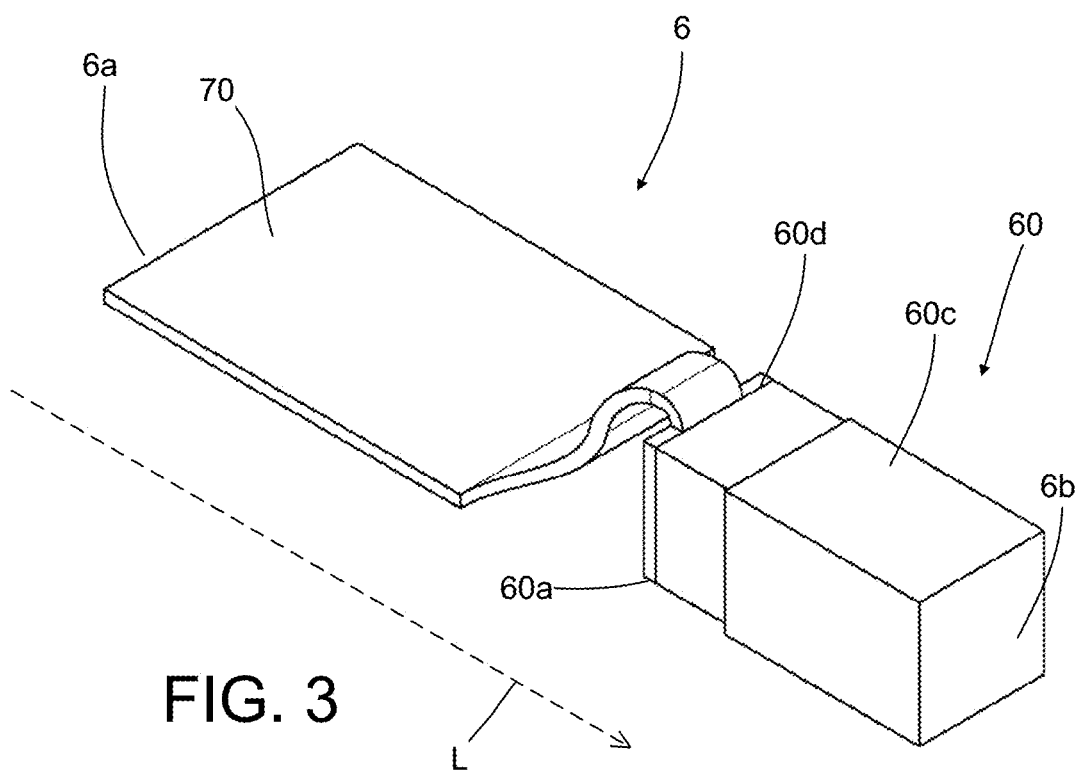
FIG. 3 shows a perspective view of the camera assembly of a tip part assembly of FIGS. 1a and 1b.
Figure 6A:
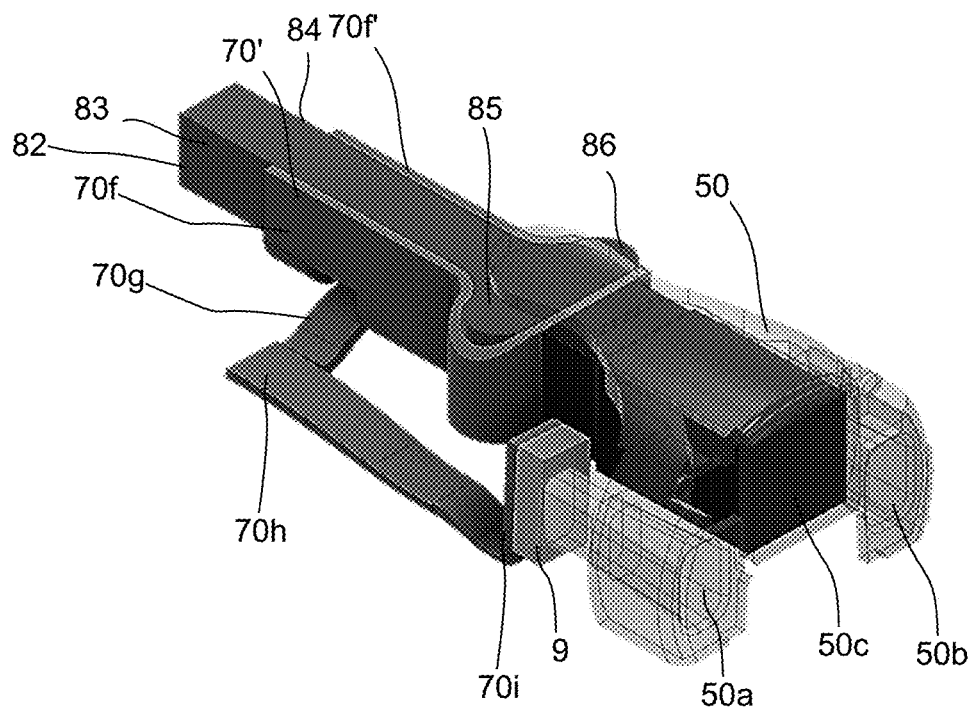
FIG. 6a shows a perspective view of an second embodiment of a camera assembly and a support of a tip part assembly.
Figure 6B:
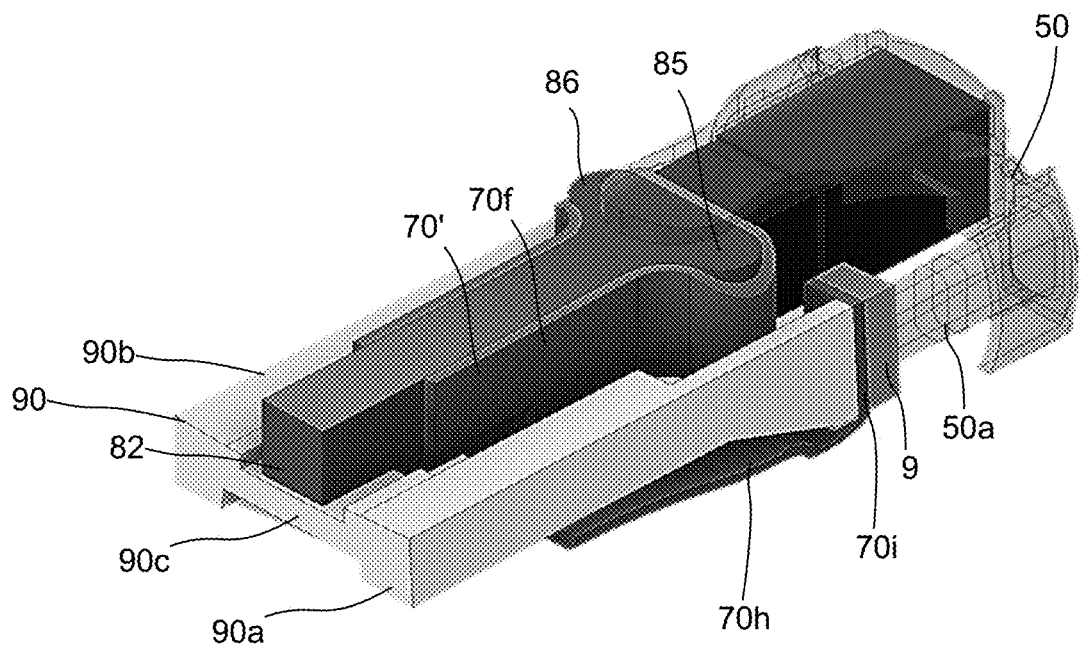
FIG. 6b shows another perspective view of the embodiment of the camera assembly and support of FIG. 6a with and an LED holder.
Figure 7A:
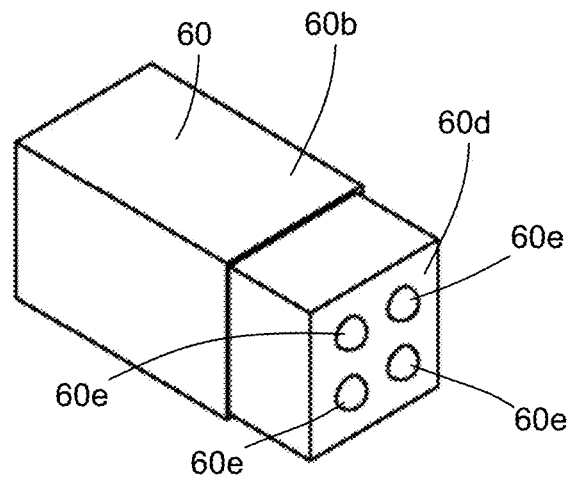
FIG. 7a is a perspective view of a camera module.
Figure 7B:
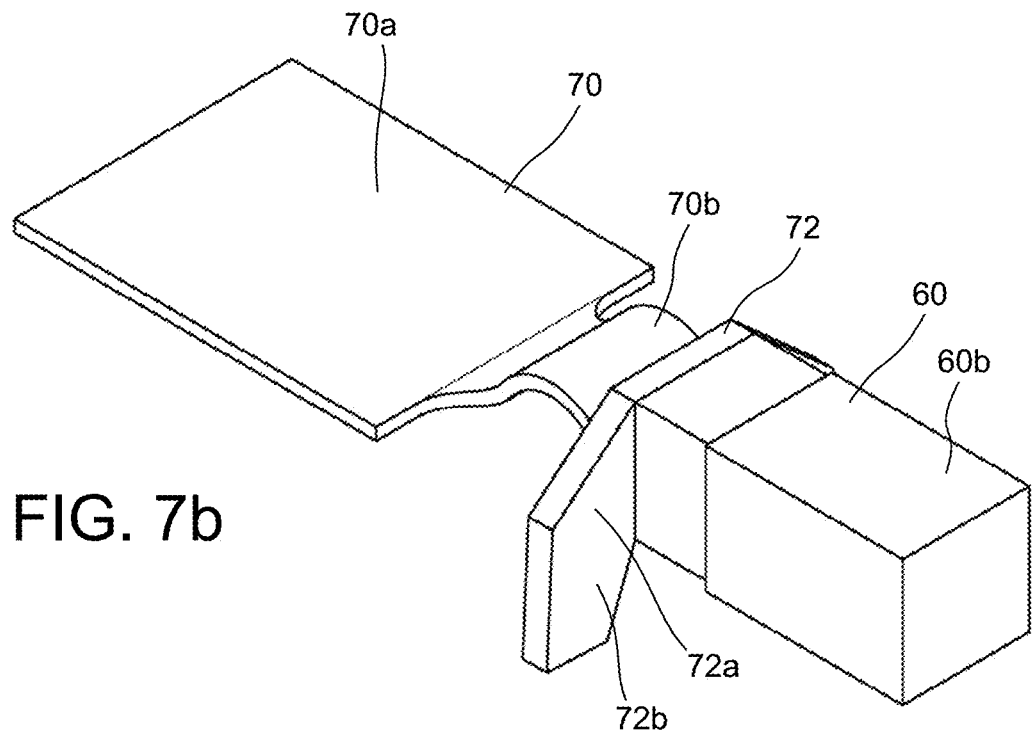
FIG. 7b is a perspective view of another embodiment of a circuit board for a camera assembly.

FIG. 3 shows a perspective view of the camera assembly 6 which is a sub-assembly of the tip part assembly 5 and comprises camera module 60 a circuit board 70 and a camera module housing 60c which house the camera module 60. The camera module 60 includes an image sensor (not shown) and a lens, which may be part of a lens stack (not shown). The camera module 60 extends in the longitudinal direction L. The circuit board 70 is electrically connected to the camera module 60 through a proximal connection surface 60d at a proximal end 60a of the camera module 60. The circuit board 70 is a flexible printed circuit (FPC). Alternatively, the circuit board 70 could be a printed circuit board (PCB). FIG. 7a shows a perspective view of the camera module 60 illustrating the proximal connection surface 60d including a plurality of connection points 60e thereon. The connection points 60e electrically connect with similarly disposed connection points on a circuit board, as shown in FIGS. 6a, 6b, and 7b.

FPCs or flex prints are well-known electronic items that can be manufactured by technologies such as flexible electronics or flex circuits. The FPC may, throughout this specification, be a single- or double-sided flexible circuit or a rigid-flex circuit and may comprise one or more layers of conductive material and two or more layers of insulating material, and/or may be a flexible flat cable having one or more conductors. It should be understood that the term "printed" is used generically to denote placement of copper layers or tracings on a substrate and does not limit a PCB to the particular method of placing the copper layers or tracings on the board. Therefore a flexible printed circuit can be described, generically, as a flexible circuit or a flexible circuit board. The flexible circuit can comprise flat cables arranged at various angles, as described below.

The outer surfaces of the camera module housing 60c are substantially box-shaped.

The lens stack also comprises a proximal lens (not shown) i.e. the lens positioned closest to the proximal end 5a of the tip part assembly 5. The camera assembly 6 is housed in the housing 8.

Figure 4A:
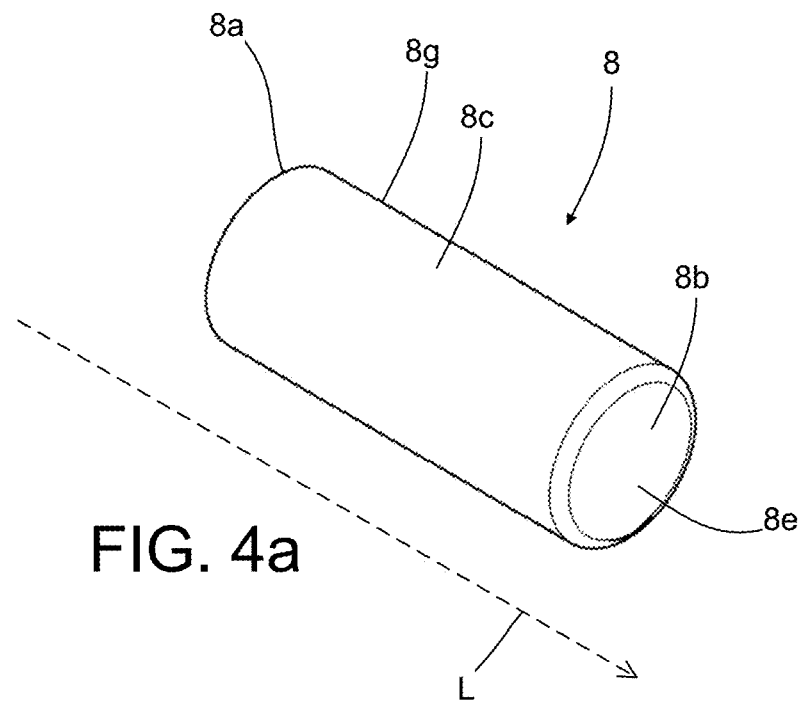
FIG. 4a shows a perspective view of a first embodiment of a tip part assembly of FIGS. 1a and 1b.
Figure 4B:
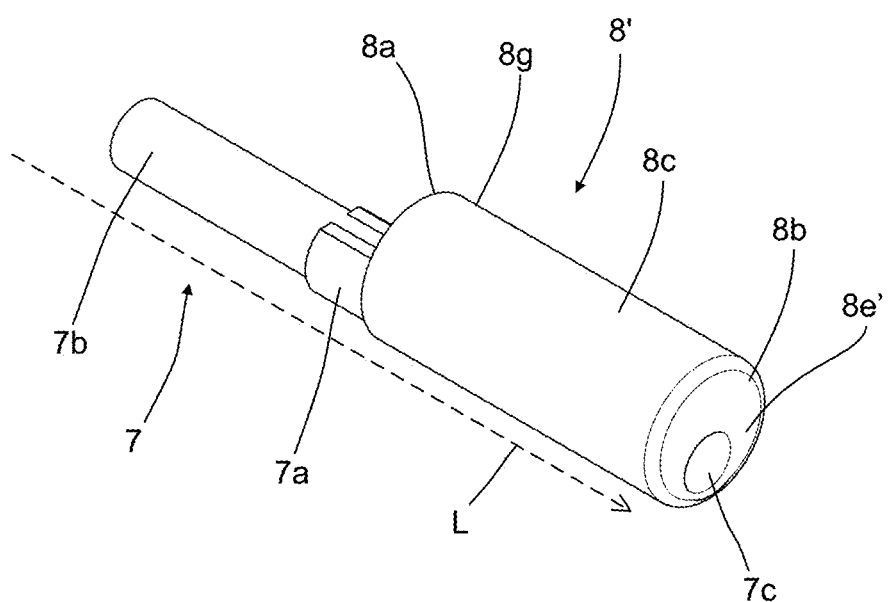
FIG. 4b shows a perspective view of a second embodiment of a tip part assembly of FIGS. 1a and 1b.
Figure 4F:
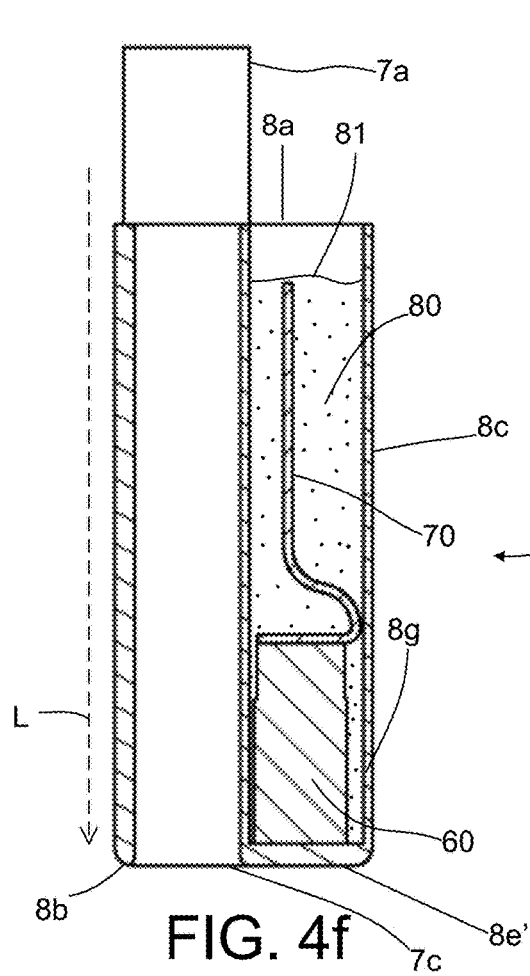
FIG. 4f shows a section view of the tip part assembly of FIG. 4d filled with an adhesive.

Referring to FIGS. 3-4f, the tip part assembly 5 is manufactured by providing the bending section 4, camera assembly 6 and cup-shaped housing 8, 8', 8" comprising a circumferential wall 8g and distal end wall 8e, 8e', 8e" enclosing a spacing as disclosed herein and inserting the camera assembly 6 through the open proximal end 8a of the housing 8, 8', 8" so that the camera assembly 6 is at least partly positioned within the spacing. Subsequent to inserting the camera assembly 6, the spacing is filled with a liquid adhesive 80 through the open proximal end 8a of the housing 8, 8', 8" so that the camera assembly 6 is at least partly embedded in the adhesive 80. The adhesive 80 is then allowed to harden whereby the adhesive 80 attaches the housing 8, 8', 8" and the camera assembly 6 whereafter the distal end segment 41 of the bending section 4 and the proximal open end 8a of the housing 8, 8', 8" are adjoined.

Turning to FIGS. 4a-4f, the cup-shaped housing 8, 8', 8" of the first, second and third embodiment of the tip part assembly are tubular and substantially cylindrical and made of polycarbonate. The outer diameter of the circumferential wall 8g of the housing 8, 8', 8" is 3.2 mm. The housing 8, 8' and 8" has a circumferentially extending outer surface 8c for facing the environment. The circumferential wall encloses a volume and extends in the longitudinal direction L between a proximal end 8a and a distal end 8b of the housing 8, 8', 8".

Where the housing 8, 8' does not comprise a hole, a window, or an opening 8f for the camera assembly 6, such as in the first and second embodiments in FIGS. 4a, 4b, 4d, 4e and 4f or a distal lens thereof (not shown), the camera assembly 6 is positioned in the housing 8, 8' with its distal end 6b adjacent to the end wall 8e, 8e' of the housing 8, 8'. The housing end wall 8e, 8e' is transparent and allows the vision sensor (not shown) of the camera assembly 6 to register an area the endoscope 1 is targeting.

Where the housing comprises a hole, a window, or an opening 8f for the camera assembly 6 or a distal lens thereof, such as the third embodiment as seen FIG. 4c, the distal end 6b of the camera assembly 6 is positioned adjacent the window 8f.

The housing 8, 8', 8" provides electrical insulation and water tightness around the circuit board 70 and electrical connections within the housing 8, 8', 8" and forms a mold or container for adhesive 80 poured into the housing 8, 8', 8". The housing 8, 8', 8" ensures that a minimum insulation thickness is present on all outer surfaces of the tip part assembly 5. The liquid adhesive 80 present in the housing 8, 8', 8", as seen in FIG. 4f, provides greater robustness, mechanical stability and rigidity of the tip part assembly, and better attachment of components within the housing 8, 8', 8". The camera assembly 6 is substantially fully embedded in the adhesive 80, except for a distal lens (not shown) thereof i.e. the lens positioned closest to the distal end 5b of the tip part assembly 5. The distal surface of the distal lens (not shown) of the camera assembly 6 is positioned adjacent a proximal surface of the housing end wall 8e, 8e'.

The liquid adhesive 80 has electrically insulating properties and is of a low dynamic viscosity below or equal to 200 cP. This helps ensure that the adhesive reaches substantially all corners of a free volume of the spacing.

In the first embodiment of the tip part assembly, a predefined amount of adhesive 80 corresponding to a desired amount of adhesive 80 in the spacing is measured off during filling. In the second embodiment an upper level 81 of the adhesive 80 is measured during filling to ensure a predefined amount of adhesive 80 is filled into the housing 8, 8', 8". The adhesive 80 also functions as a potting material and is unhardened and uncured when filling out the spacing. After the adhesive 80 has been filled into the spacing it is hardened and cured.

The housing 8, 8', 8" is an outer housing which is exterior with respect to elements housed or enclosed therein, such as the camera assembly 6, wires, electrical components, LEDs, and the like.

The method step of providing the housing 8, 8', 8" includes the step of molding the housing 8, 8', 8", which occurs before the assembly steps of the method. Molding of the housing 8, 8', 8" occurs as a two-component molding in which two different materials are molded in the same mold. The end wall 8e, 8e', 8e" of the housing 8, 8', 8" is molded in a first material, which is transparent, and the circumferential wall 8g is molded in a second, different material, which is non-transparent and includes a higher adhesive compatibility with the adhesive 80. That is, the distal end wall 8e, 8e', 8e" is formed in one piece with the circumferential wall 8g.

To improve the electrical insulation in the area around the circuit board 70 and a connection thereof to the camera assembly 6 in the housing 8, 8', 8" the wall thickness of the circumferential wall 8g increases from the distal end 8b of the housing 8, 8', 8" towards the proximal end 8a of the housing 8, 8', 8".

In the second and third embodiment shown in FIGS. 4b-4f the first portion 7a of the working channel 7 is housed in the housing 8', 8" and comprises an opening 7c in a distal surface 8e', 8e" of the housing 8', 8".

Referring to FIGS. 4b-4f, the working channel 7 has a first portion 7a with a circumferentially extending circular cylindrical outer wall enclosing a working channel spacing. The working channel 7 further comprises a second portion 7b. The second portion is connected liquid tight to the first portion 7a by an adhesive. The working channel second portion 7b extends along the proximal-distal direction PD through the insertion tube 3 to the proximal end 3a of the insertion tube 3. The second portion 7b is provided as a flexible tube.

The working channel 7 allows liquid to be removed from a body cavity or allows insertion of surgical instruments or the like into the body cavity. The working channel 7 extends from a proximal end of an endoscope to a distal end of the endoscope 1.

The working channel 7 has an inner diameter of 1.2 mm. A wall thickness of a circumferential wall of the first portion 7a of the working channel 7 is 0.2 mm. An opening 7c of the working channel 7 has a diameter of 1 mm.

The camera assembly 6 and the working channel 7 are positioned bottom-to-top.

Especially if no working channel is present, such as in FIG. 4a, the distal end wall 8e and circumferential wall 8g do not comprise any holes or openings. If the tip part assembly 5 includes a working channel 7, the working channel opening 7c is provided in the end wall 8e, 8e', 8e" such as seen in FIGS. 4b, 4e and 4f. Positioning a working channel 7 in an opening 7c in the end wall 8e, 8e', 8e" does not carry the same risk of adhesive flowing out at a periphery of the opening 7c since adhesive residuals at a working channel opening 7c are not as disruptive as is the case for adhesive residuals at the camera assembly 6, where adhesive residuals may impact vision of the camera module.

At least during the method step where the adhesive 80 is filled into the housing 8, 8', 8", the housing 8, 8', 8" is positioned so that the proximal open end 8a faces upwards. This may also be the case in the method step where the adhesive 80 is allowed to harden.

During the method step of filling the spacing with an adhesive 80, an entire free volume of the spacing is filled up with the adhesive 80 up until an upper adhesive level 81.

The tip part assembly 5 further includes LEDs 9 for illuminating a target. The LEDs are positioned in the spacing before filling adhesive 80 into the spacing. The tip part assembly 5 may include light guides 50a, 50b positioned between the distal end wall and the LEDs. The LEDs 9, and the light guides, are substantially embedded in the adhesive 80. Example light guides are shown in FIGS. 5b, 5c, 6a, 6b, and 7b.

Figure 5A:
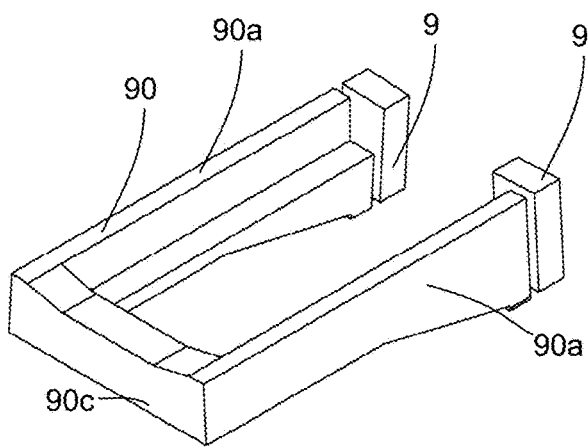
FIG. 5a shows a perspective view of a LED holder with LEDs.
Figure 5B:
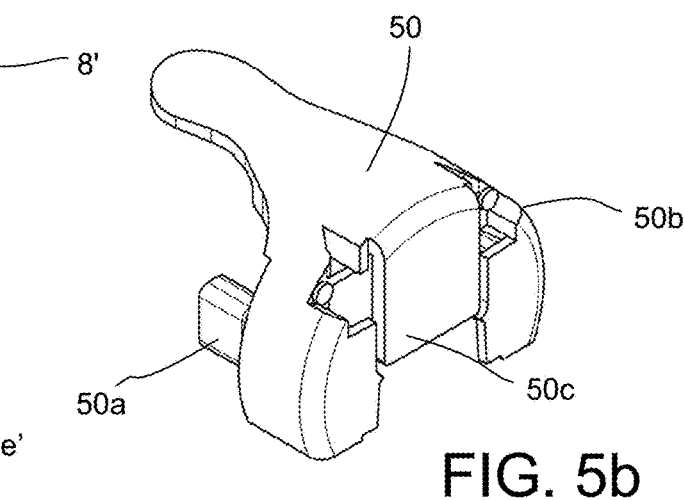
FIG. 5b shows a perspective view of a camera holder and light guide.
Figure 5C:
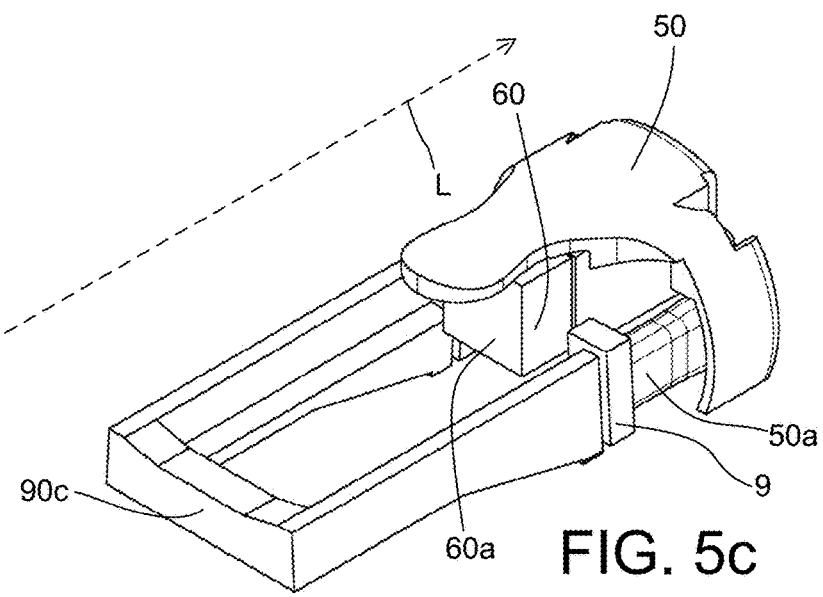
FIG. 5c shows a perspective view of an assembly of camera module in camera holder, LEDs in LED holder and light guides.

Turning to FIGS. 5a-5c, FIG. 5a is a perspective view of an LED holder 90 comprising a first portion 90a extending in the longitudinal direction L. The LED holder first portion 90a abuts an LED to ensure the LED abuts the light guide or the proximal surface of the distal end wall. A second portion 90b extends in the longitudinal direction L. The second portion 90b abuts another LED to ensure the LED abuts another light guide or the proximal surface of the distal end wall. The first and second portions 90a, 90b are interconnected by an interconnecting portion 90c. The LED holder 90 may be made from polymers selected to provide a rigid structure, such as crylonitrile butadiene styrene (ABS) and is manufactured by means of molding. The LED holder 90 is manufactured in one piece. During assembly, the camera assembly is inserted into the housing from the proximal end. The LED holder 90 can be used to push the LEDs 9, directly or indirectly, onto the light guides to ensure proper alignment and that no gaps exist that could increase reflection of light. As well as pushing the LEDs, the LED holder 90 pushes other components attached to the LEDs 9. For example, in FIG. 6b, it can be seen that the LEDs are attached to portions of a circuit board, and the first and second portions 90a, 90b of the LED holder 90 are sized and shaped to enable pushing the LEDs 9 onto the light guides 50a, 50b. In FIG. 7b, a rigid circuit board extends laterally from the proximal surface of the camera module, and (not shown) the LED holder 90 can push on the rigid circuit board thereby pushing the LEDs 9 and the camera module into its final position. In a variation, the lateral portions of the circuit board part of a flexible circuit.

FIG. 5b is a perspective view of a light passage portion 50 of the housing 8, 8'. As shown, the light passage portion 50 comprises the light guides 50a, 50b and a camera window 50c to allow the camera module 60 to capture images. The light passage portion 50 is transparent and can be molded in a two-component molding process with the circumferential wall of the housing. Distal portions of the light passage portion 50 can form part of the distal end wall 8e, 8e', 8e". Complementary portions of the distal end wall are formed with the same material used for the circumferential wall. Thus the transparent portions are formed and then non-transparent portions of the distal end wall, surrounding the transparent portions, are formed together with the circumferential wall of the housing. Alternatively, the two complementary housing portions can be made separately and adhesively bonded together. The light guides 50a, 50b can be molded in one piece with the light passage portion 50 of the housing 8, 8', 8" of the tip part assembly, as shown in FIGS. 5b and 5c. If the light guides 50a, 50b are provided separately or omitted, the light passage portion 50 comprises portions comprising LED windows to allow light from the LEDs to pass. In the assembled position, the light guides 50a, 50b extend from the distal end 5b of the tip part assembly 5 to the respective set of LEDs 9. The light guides 50a, 50b are made from a transparent material.

If no light guide 50 is present, the LED 9 may be positioned adjacent a proximal end surface of the end wall 8e, 8e', 8e", abutting the LED windows, in which case the adhesive 80 is not present between the front surface of the LED 9 and the proximal surface of the end wall 8e, 8e', 8e". If light guides 50 are present, the LED 9 may be positioned adjacent a proximal end surface of the light guides, in which case the adhesive 80 is not present between the front surface of the LED 9 and the proximal surface of the light guides.

The light guides 50 may be at least partly embedded in the adhesive 80 in the manufactured tip part assembly 5. The light guides 50 may include a light shield, in particular on a surface of the light guides 50 facing the camera assembly 6. The light shield may be provided as a layer of color or a material cladding with material having a low refraction index on said surface.

FIG. 5c is a perspective view of the light passage portion 50 of the housing assembled with the LEDs 9 and the LED support 90. The complementary, non-transparent, portion of the housing abutting the light passage portion 50 is omitted for illustration purposes.

FIGS. 6a and 6b are perspective views of a variation of camera assembly comprising a camera module support 82 having lateral surfaces 83, 84 and lateral lobes 85, 86. An FPC 70' comprises portions 70a-70f and 70f'. The FPC 70' comprises a first section including connection points and abutting the camera module. Extending laterally from the first section are two folds that abut the lobes 85, 86 of the camera module support 82. Extending from the two folds are a second section 70f and a third section 70f' that abut the lateral sides 83, 84 of the camera module support 82. A first portion 70g, a second portion 70h, and a third portion 70i of the the FPC 70' establish an electrical connection with the LEDs 9. The third portions 70i, or LED powering portions, comprise electrical connections to power the LEDs. The first portion 70g extends from and is connected to the third portion 70f' and thus extends below the camera module support 82. In a variation of the present embodiment, the first portion 70g extends from and is connected to the second portion 70f and thus does not extend below the camera module support 82. In another variation of the present embodiment, first portions 70g extend from each side and each is connected and extends from one or the other of the second portion 70f and the third portion 70f'. In a further embodiment, first portions 70 extend from the first section of the FPC 70' distally of the folds. The first, second and third portions are sized and shaped to fit within the housing allowing for various folds. The third portions 70i may be electrically connected to the LED 9 by anisotropic conductive film (ACF) bonding. All the portions and sections of the FPC 70' are formed together in one piece.

The symmetry plane S passes through the working channel and the camera module. The LEDs may be provided symmetrically on either side of the symmetry plane S.

Referring to FIG. 7b, a perspective views of another variation of a camera assembly is provided. The camera assembly comprises the camera module 60 as previously described, and a converter circuit board 72 having a first surface 72a adjacent the camera module and a second, opposite, surface adjacent the FPC 70. The FPC 70 in the present variation comprises a first portion 70a, which may be rigid, and a second portion 70b, which may be flexible and comprises a horizontal fold. The second portion 70b has connection points for electrical communication with the second side of the converter circuit board 72 and through the converter circuit board 72 with the camera module. The connection points of the connection surface 60d are arranged in a first connection point pattern. The first surface 72a of the converter circuit board 72 comprises connection points similarly arranged in the first connection point pattern. The second surface of the converter circuit board 72 comprises connection points arranged in a second connection point pattern. The second portion 70b comprises connection points arranged in the second connection point pattern. The connection points in the second connection point pattern are located lower than those of the first connection point pattern so that the fold of the second portion 70b fits within a longitudinal projection volume of the camera module. In other words, the horizontal fold is positioned below a plane passing through the upper surface of the camera module (the surface opposite the working channel) to thereby enable reduction of the radial cross-section of the housing and the endoscope.

The converter circuit board 72 also has lateral wings 72b which extend laterally from the camera module and provide mounting and connection areas for the LEDs 9 (not shown). The LED holder 90 may be used to push the lateral wings 72b and thus also the camera module into position within the housing. The LEDs may abut light guides as previously described.

During manufacture of the tip part assembly 5, the camera assembly 6 (and any variations thereof described above) and the LEDs 9 are first attached to respective circuits and holders/supports, e.g. LED holder 90 and camera module support 82, and the entire assembly is then positioned, from the proximal opening, in the housing 8, 8', 8" before filling in the adhesive 80. The holders and supports facilitate controlling the flexible circuit boards to prevent potentially damaging kinks, they can be held at the proximal ends thereof to facilitate placement of the camera module into the housing and also support during filling, and enable the assembler to maintain pressure onto the LEDs to prevent that filler finds its way between the distal surface of the LED and proximal surfaces of the light guides or the distal end windows. These benefits allow manufacture of an endoscope with very small radial cross-section.

The following additional examples expand and further exemplify the features described above:

(1) A method of manufacture of a tip part assembly for an endoscope, the tip part assembly comprising a tip part and having a proximal end and a distal end, the method comprising the steps of: providing a camera assembly of the tip part, the camera assembly including a camera module, the camera assembly having a distal end and a proximal end opposite the distal end, providing a cup-shaped housing having an open proximal end, the housing further having a distal end positioned oppositely from the proximal end and defining a distal end of the manufactured tip part assembly, the housing further comprising a circumferential wall extending between the proximal and distal ends of the housing and a distal end wall positioned at the distal end of the housing, the circumferential wall and the distal end wall enclosing a spacing, inserting the camera assembly through the open proximal end of the housing so that the camera assembly is at least partly positioned within the spacing, filling a liquid adhesive into the spacing through the open proximal end of the housing so that the camera assembly is at least partly embedded in the adhesive, allowing or causing the adhesive to harden, whereby the adhesive attaches the housing and the camera assembly to each other.

(2) A method according to (1), wherein the tip part assembly further comprises a bending section and the steps of: providing the bending section, the bending section having a distal end segment, adjoining the distal end segment of the bending section and the proximal open end of the housing.

(3) A method according to (1) or (2), wherein the camera assembly and potentially one or more LEDs are first attached to one or more holders, the interconnected holder(s) and camera assembly and potentially LED(s) then being positioned in the housing before filling in the adhesive.

(4) A method according to any one of (1) to (3), wherein the housing is positioned so that the proximal open end faces upwards.

(5) A method according to any one of (1) to (4), wherein an entire free volume of the spacing is substantially filled up with the adhesive up until an upper adhesive level.

(6) A method according to any one of (1) to (5), wherein an outer diameter of the circumferential wall of the housing is less than 3.3 mm.

(7) A method according to any one of (1) to (6), wherein a distal surface of a distal lens of the camera assembly is positioned adjacent or abutting a proximal surface of the housing end wall.

(8) A method according to any one of (1) to (7), wherein the circumferential wall and/or the end wall of the housing is transparent.

(9) A method according to any one of (1) to (8), wherein the tip part assembly further includes one or more light guides and/or LED lenses in one piece with housing.

(10) A method according to any one of (1) to (9), wherein the method includes molding the housing in a two-component molding process, wherein the end wall of the housing is molded in a first material, which is transparent, and the circumferential wall is molded in a second, different material, which is non-transparent.

(11) A tip part assembly for an endoscope, the tip part assembly comprising a tip part and having a proximal end and a distal end, the tip part assembly comprising: a tip part including a cup-shaped housing and a camera assembly positioned at least partly within a spacing of the housing, the camera assembly being attached or adhered to the housing by means of a hardened adhesive positioned within the spacing, the camera assembly being at least partly embedded in the adhesive, wherein the camera assembly includes a camera module, the camera assembly having a distal end and a proximal end opposite the distal end, wherein the housing has an open proximal end and a distal end positioned oppositely from the proximal end, the distal end of the housing defining a distal end of the tip part assembly, the housing further comprising a circumferential wall extending between the proximal and distal ends of the housing and an end wall positioned at the distal end of the housing, the circumferential wall and the distal end wall enclosing the spacing, wherein the adhesive is provided separately from the housing.

(12) A tip part assembly according to (11), further comprising: a bending section having a distal end segment, and wherein the distal end of the bending section and the proximal open end of the housing are adjoined to each other.

(13) A tip part assembly according to (11) or (12), wherein an entire volume of the spacing not preoccupied by the camera assembly and potential further components positioned in the spacing is substantially filled up with the adhesive up until an upper adhesive level, the upper adhesive level being a level of the adhesive towards the proximal end of the tip part assembly.

(14) A tip part assembly according to any one of (11) to (13), wherein an outer diameter of the circumferential wall of the housing is less than 3.3 mm.

(15) A tip part assembly according to any one of (11) to (14) wherein a distal surface of a distal lens of the camera assembly is positioned adjacent or abutting a proximal surface of the housing end wall.

(16) A tip part assembly according to any one of (11) to (15) wherein the circumferential wall and/or the end wall of the housing is transparent.

(17) An endoscope comprising a tip part assembly manufactured according to any one of (1) to (10) or a tip part assembly according to any one of (11) to (16).

(19) An endoscope comprising a tip part assembly manufactured according to any one of (1) to (10) or a tip part assembly according to any one of (11) to (16), further comprising: a converter circuit board comprising a first surface and a second surface opposite the first surface, the first surface comprising connection points arranged in the first connection point pattern and electrically connected to the connection points of the camera module, and the second surface comprising connection points arranged in a second connection point pattern; and a flexible circuit comprising connection points arranged in the second connection point pattern and electrically connected to the connection points on the second surface of the converter circuit board, wherein none of the connection points in the second connection point pattern are closer to the upper surface than a connection point in the first connection point pattern that is closest to the upper surface than other of the connection points in the first connection point pattern.

(20) An endoscope as in (19), wherein the first connection point pattern comprises four connection points arranged in a respective corner of a substantially rectangular shape, and wherein the second connection pattern comprises four connection points arranged along a substantially straight line.

(21) An endoscope as in (19), wherein the flexible circuit includes a first portion positioned face-to-face with the converter circuit board and a second portion extending from the first portion and comprising a first fold extending toward a proximal end of the housing, wherein the second portion does not extend above a plane passing through the upper surface of the camera module.

(22) An endoscope comprising a tip part assembly manufactured according to any one of (1) to (10) or a tip part assembly according to any one of (11) to (16), further comprising: a flexible printed circuit, wherein the flexible printed circuit comprises a first portion overlapping the proximal connection surface of the camera module and a first fold extending laterally from the first portion and toward the proximal end.

(23) An endoscope as in (22), wherein a symmetry plane passes through a longitudinally extending centre line of the working channel and through the camera module, wherein the flexible printed circuit comprises a second portion extending proximally from the first fold.

(24) An endoscope as in (23), further comprising a flexible printed circuit support having a proximal end and a distal end, the proximal end comprising a longitudinal portion having lateral surfaces and the distal end including a first lobe and a second lobe extending laterally on opposite sides of the symmetry plane, wherein the first fold curves about the first lobe and the second section abuts one of the lateral surfaces of the longitudinal portion.

(25) An endoscope as in (23), wherein the endoscope includes a housing enclosing a volume and having a circumferentially extending outer surface extending in the longitudinal direction, the working channel being at least partly housed in the housing and comprising an opening in a distal surface of the housing, the camera assembly being at least partly housed in the housing.

LIST OF REFERENCES

The following is a list of reference numerals used throughout this specification.
1 endoscope
11 monitor
12 cable socket
13 monitor cable
2 handle
21 control lever
3 insertion tube
3a proximal end
3b distal end
4 bending section
41 distal end segment
42 intermediate segment
43 proximal segment
5 tip part assembly
5a tip part assembly proximal end
5b tip part assembly distal end
50 light passage portion
50a, light guide
50b
50c camera window
6 camera assembly
6a camera assembly proximal end
6b camera assembly distal end
60 camera module
60a camera module proximal end
60c camera module housing
60d camera module connecting surface
7 working channel
7a first working channel portion
7b second working channel portion
7c working channel hole or opening
70 circuit board
8 housing
8' housing
8''' housing
8a housing proximal end
8b housing distal end
8c outer surface
8e housing end wall
8e' housing end wall
8e'' housing end wall
8f window
8g circumferential wall
80 liquid adhesive
81 adhesive level
9 light-emitting diode (LED)
90 LED holder
82 Camera holder
L longitudinal direction
PD proximal-distal direction

The invention claimed is:

1. A method to manufacture an endoscope, the method including:
  providing a camera assembly including a camera module, light emitting diodes (LEDs), a flexible circuit or circuit board having a first portion disposed adjacent a proximal surface of the camera module and LED powering portions connected to the LEDs, and an LED holder having first and second longitudinal portions extending from an interconnecting portion, the camera assembly having a distal end and a proximal end opposite the distal end, and the camera module including a distal lens having a distal surface;
  providing a housing having a proximal end opposite a distal end, a distal end wall at the distal end, and a circumferential wall connected to the distal end wall and extending from the distal end wall to the proximal end of the housing, the circumferential wall and the distal end wall defining a spacing of the housing, the distal end wall comprising a camera window having a proximal surface;
  connecting the first portion to the camera module, and attaching the LED powering portions onto distal ends of the first and second longitudinal portions of the LED holder;
  after connecting the first portion to the camera module, inserting at least part of the camera assembly through the proximal end of the housing into the spacing to position the distal surface of the distal lens adjacent to and longitudinally aligned with the proximal surface of the camera window of the distal end wall of the housing;
  filling at least a portion of the spacing with a liquid adhesive through the proximal end of the housing to at least partly embed the camera assembly in the liquid adhesive; and
  allowing or causing the liquid adhesive to harden to attach the housing and the camera assembly to each other.

2. The method of claim 1, wherein the distal end wall comprises light guides, wherein inserting at least part of the camera assembly comprises pushing the LED holder until distal surfaces of the LEDs abut proximal surfaces of the light guides.

3. The method of claim 1, further comprising holding the housing with the proximal end facing upward during filling the at least the portion of the spacing with a liquid adhesive.

4. The method of claim 3, wherein an entire free volume of the spacing is substantially filled up with the adhesive up until an upper adhesive level.

5. The method of claim 1, further comprising manufacturing the housing with a transparent material at the distal end wall and a non-transparent material at the circumferential wall.

6. The method of claim 5, wherein manufacturing the housing comprises injecting a transparent material into a mold and subsequently injecting a non-transparent material into the mold.

7. The method of claim 1, wherein an outer diameter of the circumferential wall of the housing is less than 3.3 mm.

8. The method of claim 1, wherein the distal surface abuts the proximal surface of the camera window of the distal end wall of the housing.

9. The method of claim 8, wherein the circumferential wall comprises non-transparent material and at least a portion of the distal end wall of the housing is transparent.

10. The method of claim 1, wherein prior to providing the housing the method comprises molding the housing in a two-component molding process, wherein at least a portion of the end wall of the housing is molded in a first material, which is transparent, and the circumferential wall is molded in a second, different material, which is non-transparent.

11. A method to manufacture an endoscope, the method including:
- providing a camera assembly including a camera module, an LED holder, light emitting diodes (LEDs), a flexible circuit or circuit board having a first portion disposed adjacent a proximal surface of the camera module and LED powering portions connected to the LEDs, the LED holder comprised of polymeric material and having an interconnecting portion and first and second longitudinal portions extending distally from the interconnecting portion, the camera assembly having a distal end and a proximal end opposite the distal end, the camera module including a distal lens having a distal surface;
- providing a housing having a proximal end opposite a distal end, a distal end wall at the distal end, and a circumferential wall connected to the distal end wall and extending from the distal end wall to the proximal end of the housing, the circumferential wall and the distal end wall defining a spacing of the housing, and the distal end wall comprising a camera window having a proximal surface;
- connecting the first portion of the flexible circuit or circuit board to the camera module and attaching the LED powering portions onto distal ends of the first and second longitudinal portions of the LED holder;
- after connecting the first portion to the camera module, inserting at least part of the camera assembly through the proximal end of the housing into the spacing and positioning the distal surface adjacent to and longitudinally aligned with the proximal surface of the camera window of the distal end wall of the housing;
- while holding the housing with the proximal end facing upward, filling at least a portion of the spacing with a liquid adhesive through the proximal end of the housing to at least partly embed the camera assembly in the liquid adhesive; and
- allowing or causing the liquid adhesive to harden to attach the housing and the camera assembly to each other,
- wherein inserting at least part of the camera assembly comprises pushing the interconnecting portion of the LED holder to position the distal surface of the distal lens adjacent to and longitudinally aligned with the proximal surface of the camera window.

12. The method of claim 11, wherein the inserting the at least part of the camera assembly includes inserting the at least part of the camera assembly until the distal surface abuts the proximal surface of the camera window of the distal end wall of the housing.

13. The method of claim 11, wherein the distal end wall comprises light guides, and wherein pushing the interconnecting portion of the LED holder to position the distal surface adjacent to and longitudinally aligned with the proximal surface comprises pushing the interconnecting portion until distal surfaces of the LEDs abut proximal surfaces of the light guides.

14. The method of claim 11, further comprising:
- providing a camera module support extending from a distal end to a proximal end;
- placing the distal end of the camera module support against the second portion of the flexible circuit or circuit board; and
- placing the proximal end of the camera module support onto the interconnecting portion of the LED holder before pushing the interconnecting portion of the LED holder to position the distal surface adjacent to and longitudinally aligned with the proximal surface.

15. The method of claim 11, wherein the camera module comprises electrical connection points, wherein connecting the first portion of the flexible circuit or circuit board to the camera module comprises electrically connecting the connection points of the camera module with corresponding connection points of the flexible circuit or circuit board, and wherein the connection points of the camera module consist of four electrically connecting points.

16. The method of claim 15,
- wherein the camera assembly includes a converter circuit board having a first surface adjacent the camera module and a second, opposite, surface adjacent the flexible circuit or circuit board, the first surface including connection points disposed in a first pattern and the second surface including connection points disposed in a second pattern,
- wherein the connection points of the camera module are disposed in the first pattern,
- wherein the flexible circuit or circuit board includes a first portion and a second portion proximal of the first portion, the second portion including the connection points and a horizontal fold intermediate the connection points and the first portion, the connection points on the second portion being disposed in the second pattern,
- wherein the camera module has an upper surface and a lower surface opposite the upper surface, the horizontal fold being located below a plane passing through the upper surface, and
- wherein the connection points in the second pattern are positioned further away from the plane than the connection points in the first pattern.

* * * * *